United States Patent [19]
Claridge et al.

[11] 3,942,019
[45] Mar. 2, 1976

[54] ELECTRON COLLIMATOR

[75] Inventors: Geoffrey Maximilian Lawrence Claridge; Brian Sydney Driver; Timothy Robert Jarvis, all of Sussex, England

[73] Assignee: U. S. Philips Corporation, New York, N.Y.

[22] Filed: Apr. 24, 1974

[21] Appl. No.: 463,676

[30] Foreign Application Priority Data
Apr. 17, 1973 United Kingdom............... 18438/73

[52] U.S. Cl.............................. 250/512; 138/157
[51] Int. Cl.².... A61N 5/10; G21F 5/04; G21K 1/04
[58] Field of Search ........ 250/505, 511, 512; 220/8, 220/22.1; 350/60; 138/156, 157, 177, 178

[56] References Cited
UNITED STATES PATENTS

| | | | |
|---|---|---|---|
| 1,212,948 | 1/1917 | Hesse................................... | 220/8 |
| 2,049,184 | 7/1936 | Walsleben............................ | 138/157 |
| 2,675,486 | 4/1954 | Green et al.......................... | 250/512 |
| 2,840,257 | 6/1958 | Zeni...................................... | 220/8 |

Primary Examiner—Archie R. Borchelt
Assistant Examiner—T. N. Grigsby
Attorney, Agent, or Firm—Frank R. Trifari; Leon Nigohosian

[57] ABSTRACT

An electron collimator is formed by two pairs of multi-leaved corner plates which are capable of simultaneous movement to alter the dimension of the collimator in two dimensions.

In a preferred embodiment each corner shaped plate has two leaves which interleave with the leaves of an adjoining corner plate.

5 Claims, 4 Drawing Figures

ELECTRON COLLIMATOR

The present invention relates to electron collimators and more particularly to electron collimators for use in radiotherapy apparatus.

In known radiation apparatus the electron-beam cross sectional dimensions are defined by a number of fixed collimators or collimating systems.

The present invention provides a collimating system which can vary the electron beam cross section in two directions, while retaining the advantage of completely enclosing the beam as with conventional fixed dimension collimators.

Figure 1:
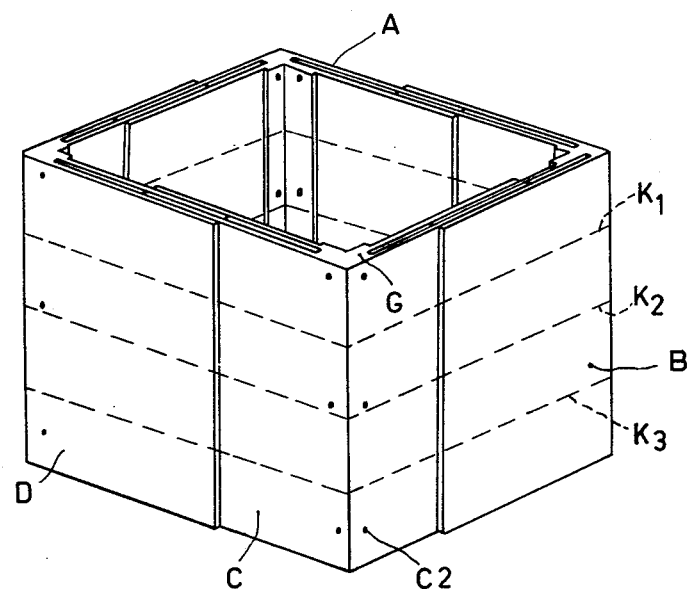
Figure 3:
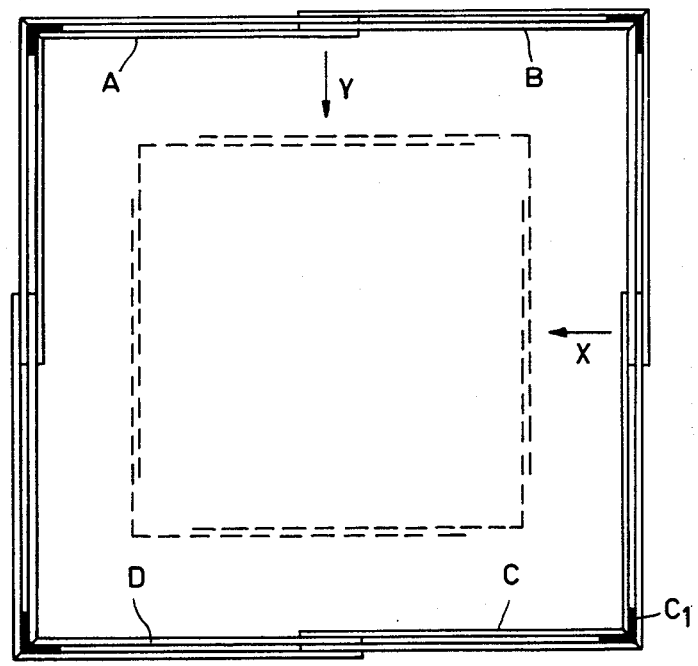
Figure 2:
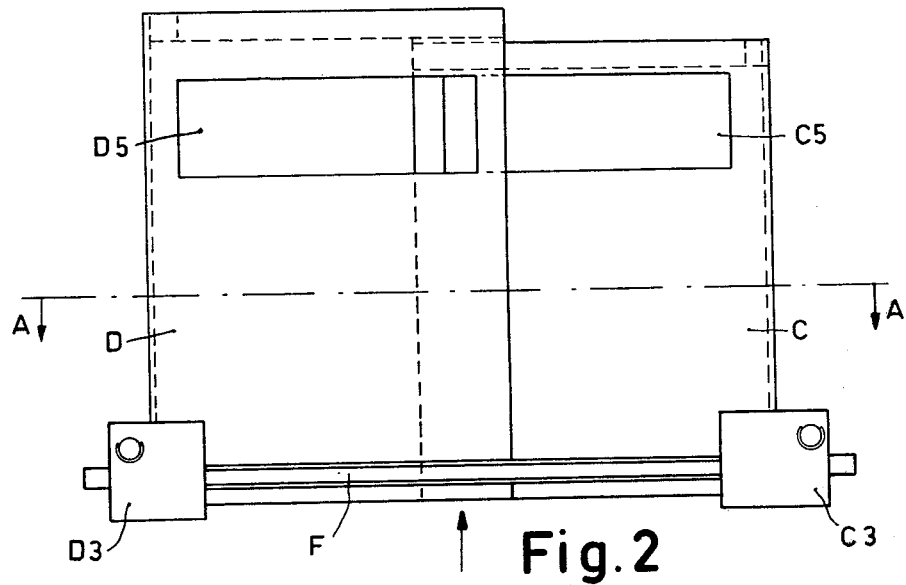
Figure 4:
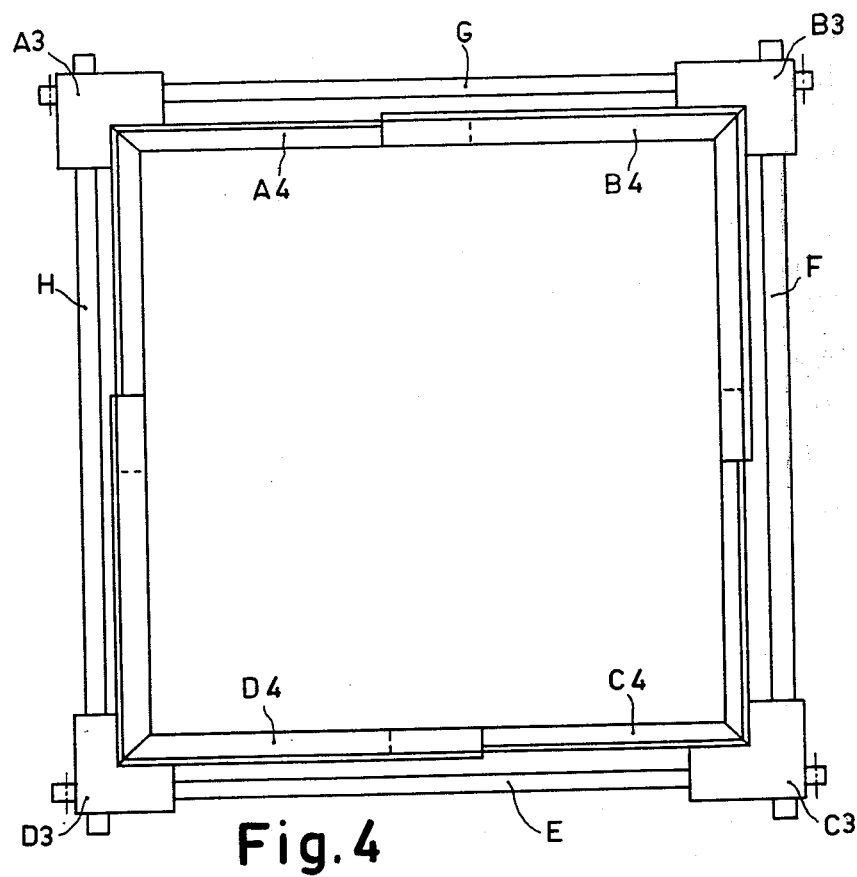

The present invention will now be described, by way of example with reference to the accompanying drawings, in which:

FIG. 1 shows a perspective view showing the principle of a collimator according to the present invention, FIG. 2 shows one side elevation of the apparatus of FIG. 1, FIG. 3 shows a cross section along line A—A of FIG. 2, FIG. 4 shows a plan view from above of the apparatus of FIG. 2.

Referring now to FIG. 1 of the drawings, a pair of complex plates or wall portions A and C which are substantially identical to each other are interleaved with a pair of plates or wall portions B and D which are substantially identical with each other. The four plates A, B, C, D form a square or rectangular opening or open box as shown more clearly in FIG. 3.

Each plate A, B, C or D is constructed so as to form two wall structures, i.e., half sides of the open box. Each side or half of each plate comprises two sheets of metal which may be considered to be fingers which co-operate or interlace with the fingers of a further plate to form a barrier which the electrons cannot easily penetrate. The complex plates may be constructed as shown in FIGS. 1 and 3 with spacing pieces C1 and rivetted together with rivets C2. They can also be made by any other suitable mechanical construction, e.g. by welding.

In FIG. 3 the plates A, B, C and D are shown in their positions in which the open box is a maximum size it being noted that a certain amount of interlace is still present to prevent penetration by the electrons.

The dotted lines indicate the minimum size of the open box construction which is obtained when the interlacing between the plates is at a maximum. Intermediate positions are obtained by moving the plates in the directions X and Y as indicated in FIG. 3.

Referring now to FIG. 2 the end elevation shows half of plates C and D. A mechanism for moving the plates C and D is shown which may consist for example of a threaded rod E with left and right hand threads either side of its longitudinal mid point and attached to plates C and D by journals within gear boxes C3 and D3. Thus on rotation of rod E the plates C and D will move either towards or away from each other depending on the direction of rotation. By suitable gearing within the gearboxes A3, B3, C3 and D3 the plates A, B, C and D can be moved in unison.

The direction of the electron beam is indicated by an arrow in FIG. 2.

From FIG. 2 it is seen that the plates D and C need not be of the same height, plate D being taller than plate C. Similarly plate B will in this arrangement be taller than plate A. The reason for this is evident from FIG. 4 in which beam distribution correctors A4, B4, C4 and D4 are shown. Thus the wall portion $B_4$, which act as a beam deflector can slide in a plane above that of the wall portion $A_4$ which acts as a beam deflector and which can slide internally within the box structure.

In FIG. 2 openings D5, C5 are shown in the plates D and C. These may be provided to permit a view of the internal field.

When the box like structure is a minimum size a gap is left on its outside which can allow the passage of the electron beam. This gap can be closed by mounting plates similar to the beam distribution correctors A4, B4, C4, D4 on the outside walls of the plates A, B, C and D to block the flow of electrons as the size of the box is contracted.

The plates A, B, C and D in a practical embodiment require bearings or bearing surfaces on which to move. These may be provided by any means suitable for supporting the mechanical stresses in accordance with the size and weight of the completed structure.

In a specific embodiment according to the invention the plates A – D are all subdivided in mutually isolated sheets dividing the box as shown in FIG. 1, going from top to bottom there, into piled-up flattened boxes. By this a constrictable collimator having a focussing action can be realised. In a practical embodiment each plate may be divided into 4 sheets.

What is claimed is:

1. An electron beam collimating device, comprising an open ended structure having a substantially rectangular shape, said structure comprising four wall portions of which at least parts are substantially electron impermeable, said wall portions being interlaced with and movable relative to each other and defining a passageway for said beam, each of said wall portions comprising first and second wall structures angularly disposed with respect to each other.

2. An electron beam collimating device as in claim 1, wherein each of said wall structures comprises joined plural sheets that are interlaced with the respective sheets of another one of said wall structures, said wall structures comprising respective unitary bodies.

3. An electron beam collimating device as in claim 2, where said wall structures individually comprise a double sheet structure.

4. An electron beam collimating device as in claim 1, wherein said wall structures comprise openings via which the interior of said device is accessible.

5. An electron beam collimating device as claimed in claim 1, comprising plural walls and each of said walls comprises two corresponding adjacent said wall structures.

* * * * *